(12) United States Patent
Zorin et al.

(10) Patent No.: US 8,790,890 B2
(45) Date of Patent: Jul. 29, 2014

(54) DIAGNOSTIC METHOD FOR CONNECTIVE TISSUE AND ITS APPLICATION

(75) Inventors: Vadim Leonidovich Zorin, Moscow (RU); Alla Ivanovna Zorina, Moscow (RU); Vladimir Ryurikovich Cherkasov, Moscow (RU); Pavel Borisovich Kopnin, Moscow (RU)

(73) Assignee: Obshhestvo S Organichennoi Otvetstvennost' Yu "Vitacel", Moscow (RU)

( * ) Notice: Subject to any disclaimer, the term of this patent is extended or adjusted under 35 U.S.C. 154(b) by 0 days.

(21) Appl. No.: 13/992,962

(22) PCT Filed: Sep. 6, 2012

(86) PCT No.: PCT/RU2012/000745
§ 371 (c)(1),
(2), (4) Date: Jun. 10, 2013

(87) PCT Pub. No.: WO2013/051963
PCT Pub. Date: Apr. 11, 2013

(65) Prior Publication Data
US 2013/0266550 A1    Oct. 10, 2013

(30) Foreign Application Priority Data
Oct. 3, 2011    (RU) .............................. 2011140055

(51) Int. Cl.
*G01N 33/48* (2006.01)
*A61B 5/00* (2006.01)
*C12N 5/07* (2010.01)
*C12N 5/071* (2010.01)
*C12N 5/22* (2006.01)

(52) U.S. Cl.
USPC ............... 435/29; 435/325; 435/366; 702/19

(58) Field of Classification Search
None
See application file for complete search history.

(56) References Cited

U.S. PATENT DOCUMENTS 7,991,557 B2 *    8/2011    Liew et al. ...................... 702/19

FOREIGN PATENT DOCUMENTS

| GB | 2 347 223 | 3/2003 |
|---|---|---|
| GB | 2 395 489 | 5/2004 |
| RU | 2 008 020 | 2/1994 |
| RU | 2 017 818 | 8/1994 |
| RU | 2 045 478 | 10/1995 |
| RU | 2 054 009 | 2/1996 |
| RU | 2 087 913 | 8/1997 |
| RU | 2 107 296 | 3/1998 |
| RU | 2 110 798 | 5/1998 |
| RU | 2 161 653 | 1/2001 |
| RU | 2281776 | 8/2006 |
| RU | 57576 | 10/2006 |
| RU | 2418571 | 5/2011 |
| RU | 2428996 | 9/2011 |
| SU | 1372216 | 2/1988 |
| WO | 00 11473 | 3/2000 |
| WO | 03 019171 | 3/2003 |
| WO | 2008 110570 | 9/2008 |

OTHER PUBLICATIONS

Akudugu et al. "Clonogenic survival and cytokinesis-blocked binucleation of skin fibroblasts and normal tissue complications in soft tissue sarcoma patients treated with preoperative radiotherapy", Radiotherapy and Oncology 72: 103-112, 2004.*
Belyaeva, A. Yu., "Disorders of Proliferative Potential of Derman Fibroblasts in Skin Ageing," Siberian State Medical University, Tomsk, International Scientific Student Conference n.a. N.I. Pirogov No. 64, Total pp. 6, (Tomck 2005) (with English translation).
Luzina, L. I., "Computer Modeling," Textbook, State University of Tomsk, p. 8, paragraph 1, Total pp. 3, (2001) (with partial English translation).
Vladimirskaia, EB, et al., "Stromal fibroblasts of normal bone marrow in children," Gematol Transfuziol, vol. 35 (1), pp. 3 to 5, (Jan. 1990) (with English abstract).
Written Opinion of the International Searching Authority Issued Jan. 25, 2013 in PCT/RU12/00745 Filed Sep. 6, 2012 (with English translation).
International Search Report Issued Feb. 14, 2013 in PCT/RU12/00745 Filed Sep. 6, 2012.

* cited by examiner

*Primary Examiner* — Ruth Davis
*Assistant Examiner* — Emily Cordas
(74) *Attorney, Agent, or Firm* — Oblon, Spivak, McClelland, Maier & Neustadt, L.L.P.

(57) ABSTRACT

The present invention relates to medicine and is used to evaluate conditions and to detect connective tissue pathology (and/or organ) by clonal analysis. The present invention relates to aesthetic medicine and is used for correction of aging skin changes. The method includes: cultivation of substrate-dependent cell colonies of analyzed tissue and/or organ, at conditions which provide formation of discrete colonies applicable for visualization, statistically reliable analysis of derived colonies, determination of at least one parameter which characterizes regenerative potential of population of substrate dependent cells, determination of at least one parameter which characterizes proliferative potential of population of substrate dependent cells, and processing of obtained results which allows to evaluate regenerative ability of patient's tissue and/or organ. The method provides objective qualitative characteristics of both the proliferative and regenerative potential which allows evaluating the regenerative potential of primary tissue (and/or organ) without complex and expensive instrumental studies. A computer based system for performing the present method is also provided.

4 Claims, 9 Drawing Sheets

DIAGNOSTIC METHOD FOR CONNECTIVE TISSUE AND ITS APPLICATION

BACKGROUND OF THE INVENTION

1. Field of Invention

The invention is in the field of medicine and can be used to assess status or detect connective tissue (and/or organ) pathology by means of clonal analysis of substrate-dependent cells forming the tissue. In particular, the invention relates to aesthetic medicine and can be used for dermal examination and subsequent individual correction of aging and other structural skin changes. The methods of the present invention for evaluation of cell populations (in particular, a fibroblast population) forming connective tissue can be used for examining conditions, pathologies and any changes which are determined, mediated or otherwise related to particularities of regenerative processes occurring in such tissue (and/or organs). The methods are also applicable to prediction of the treatment efficacy, correct changes and pathologies which outcome depends upon regenerative processes, their intensity and duration.

2. Discussion of the Background

A method for analyzing cell aging by the identification of changes in biological parameters of the cells, such as characteristics of cell metabolism under the influence of aging factors, is described in GB2395489 (IPC C12N5/06). This method includes proteomic, genomic, and/or transcriptomic investigations or a combination thereof with the subsequent comparison of the results obtained from such investigations for (i) "young" cells, i.e., cells derived from a young donor, with a few (e.g., 1-5) in vitro culturing passages or cells obtained from a tissue with the minimal exposure to UV radiation, and (ii) "old" cells derived from elderly donors or cells with many (more than 7) in vitro passages or cells from a tissue exposed to high UV radiation, wherein cell cultures are placed in a three-dimensional matrix mimicking biological a tissue (e.g., connective, epithelial, and epidermal tissue). This method is proposed for screening studies for identification of pharmaceutical agents capable of modulation of metabolic processes in aging cells.

Among the drawbacks of this method is its complicated execution and that it requires highly qualified personnel and specialized expensive equipment, which stands in the way of the routine use of the method, especially in practicing esthetic medicine. Furthermore, this method is confined to using only cells in vitro and cannot be used to characterize conditions of a cell population from tissue in vivo, from which such cells are obtained, and, consequently, this method cannot be used for diagnosis of tissues on the cellular level and prognosis of a subsequent treatment method.

A method of determining colony forming units (CFU) of endothelial progenitor cells by characterizing cell preparations for the use in regenerative medicine or clinical transplantology is described in WO 2008110570 (IPC G01N33/50, C12N5/06). This publication describes a method of analyzing influence of substances and conditions of performing the analysis on CFU values of endothelial progenitor cells for the subsequent use as a screening test for identifying a positive or negative influence of individual substances on the proliferation of endothelial progenitor cells. This method involves explanation of the initial cells in a suitable medium with a density preventing contact inhibition of growth of the cells, followed by incubation of the cells for several days and analysis of the formed colonies. This analysis of the colonies was carried out by staining, counting, and ranking colonies by size into two groups. One group included colonies of the cells with the high proliferative potential, wherein the colonies were larger than a particular threshold value, equal to 2-4 mm, depending on a composition of the medium, while the other group included colonies with the normal and low proliferative potential, wherein the size of the colonies was equal to or less than the threshold value.

The drawback of this method is that it could be only used for analyzing endothelial progenitor cells, e.g., human umbilical cord endothelial cells (HUVEC) and human microvascular endothelial cells. Also, this method can be used for studying cells in vitro but cannot be used for characterizing conditions of a cell population of tissue in vivo, from which such cells are derived, and, therefore, it cannot be used for diagnosis of tissue on the cellular level and prognosis of a subsequent treatment method.

The method for analyzing a population of fibroblasts from the skin and muscle tissue of 7-8 week human embryos, which involves trypsinization of the cells, and explanation and incubation in a nutrient medium with the subsequent counting of pleomorphic, spindle- and sail-like cells, is described in RU 2017818 (IPC C12N5/02). This method analyzes postnatal cultures of dermal fibroblasts in regard to their mitotic activity by counting colonies with the certain number and density of the cells.

The drawbacks of this method are its labor intensiveness, the need for special equipment, and subjective and qualitative nature of the obtained results, which makes the interpretation of the results difficult and limits their practical application.

The prognostic method for distraction osteogenesis is proposed in patent RU 2110798 (IPC G01N33/48). The method includes implanting culture of bone marrow cells, for example, isolated from sternum, of an experimental animal or human subject in diffusion chambers into mice. After 7 days, the chambers were withdrawn, and their content was used for cytological preparations in which the number of clusters and monocyte-macrophage and fibroblast colonies were calculated. Based on their ratio, the prognostic index (PI) was calculated, and if PI was >1, abnormalities in bone formation were predicted. The authors declare that the method is low traumatic and allows detecting early term abnormalities in the bone formation which are related to disorders of the immunological regulation of distraction osteogenesis.

The disadvantages of this method include highly specialized orientation (prognosis of distraction osteogenesis based on the number of bone marrow clonogenic cells) which limits the use of the method for studying regenerative processes in other tissues and organs. Moreover, the method requires using a great number of laboratory animals (up to 6 mice per one study), involving, besides ethical problems, the necessity to keep a specialized vivarium and availability of operative qualified personnel that significantly increases the cost and complicate the proposed method.

The prognostic method is also known for surgical treatment of chronic osteomyelitis [SU 1372216, IPC G01N1/28] which includes biopsy, cell isolation and cultivation with subsequent calculation of the grown bone marrow fibroblasts. To increase accuracy of the method, after the biopsy from the osteomyelitis locus, the material is transferred to a media 199 with antibiotics for 12-24 hours, and the cloning efficiency of the bone marrow stromal cells is calculated by the formula: $CE = a*100000/n$, where: CE=cloning efficiency; a is the number of the grown colonies; n is the number of the bone marrow cells, and when CE values are not greater than 5, they predict the poor outcome of the postoperative period, and when CE values are 5.1-100000, the outcome is favorable.

As it follows from the description, the invention suggests the diagnostic use of only one parameter—cloning efficiency of the cells which are isolated immediately from patient's bone tissue. In particular, in contrast to the method of the present invention, the method of SU 1372216 provides only the analysis of well-defined colonies, without considering their distribution per the cell density and the presence of sub-visible diffuse colonies which may contain essential diagnostic information. The above-mentioned parameter of the cloning efficiency equally depends upon two complementary values, i.e., the number of cells which while cultivated are able to form colonies (so called colony-forming units-fibroblast, CFU-f), and the proliferative activity of such CFU-f (i.e., colony forming rate). Calculation of only well-formed colonies can result in underestimation and, finally, distortion of the results. Moreover, available experimental data show seasonal variations of the proliferative activity of the bone marrow cells which undermine reproducibility of the results that make the patent authors to take additional measures to provide a high proliferative activity of the cells, in particular, to use animal feeder cells which reduce feasibility and increase production cost of the method.

BRIEF DESCRIPTION OF DRAWINGS

FIG. 3. Illustration of the dependency of the proportion of diffuse colonies at the instrumental assessment stage of the wrinkle depth (VISIA®, Proctor&Gamble Co, USA).

FIG. 4. Illustration of the dependence of the proportion of dense colonies on patient's skin elasticity (CUTOMETER® MPA 580, Courage+Khazaka electronic GmbH, Germany).

FIG. 5. Illustration of the dependence of the proportion of diffuse colonies on patient's skin elasticity (CUTOMETER® MPA 580, Courage+Khazaka electronic GmbH, Germany).

DETAILED DESCRIPTION OF THE INVENTION

Figure 1:
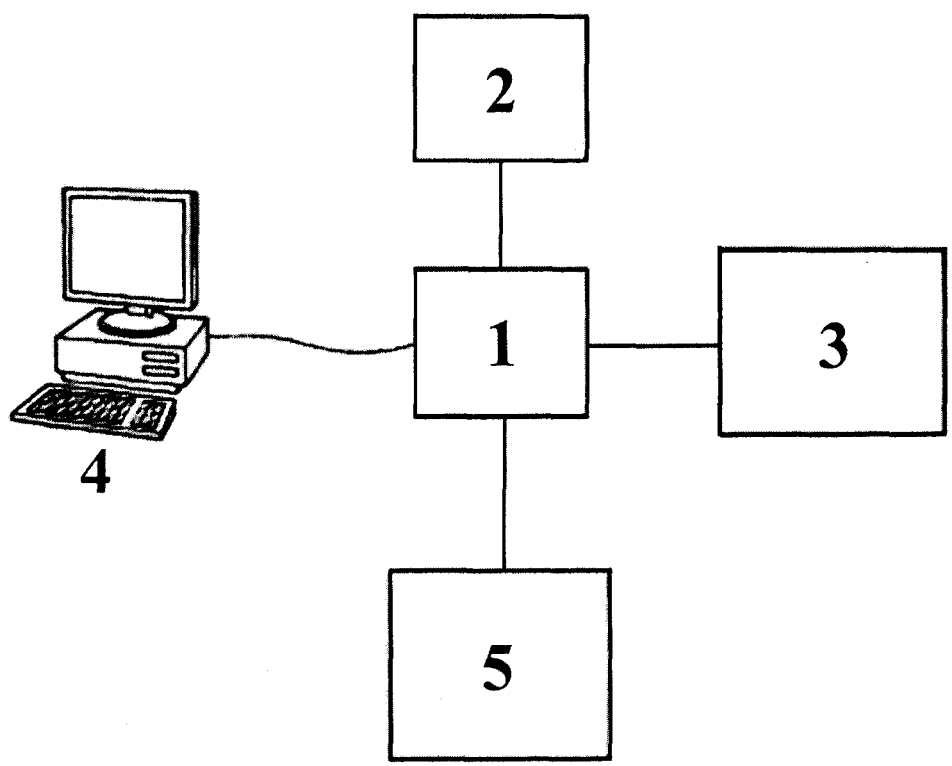
FIG. 1. A principal scheme of the proposed computer system.
Figure 2:
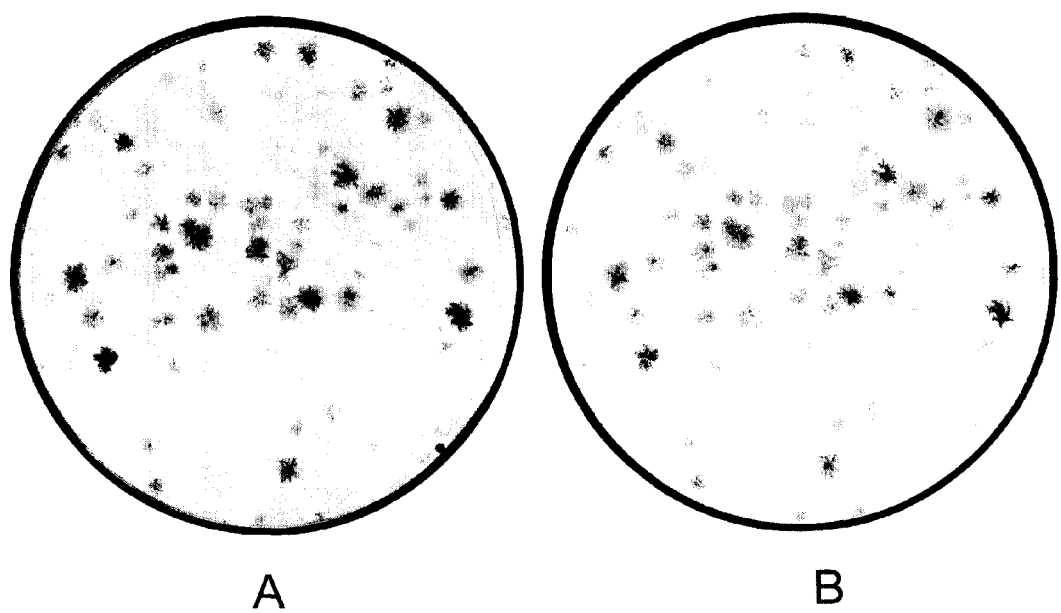
FIG. 2. An electronic image of typical patient colonies (A) and the results of their computer processing for the morphometric analysis (B).

The methods of the present invention include evaluate status and/or detection of connective tissue pathology and are based on the determination of the regenerative and proliferative potentials of the cells forming the tissue—fibroblasts—which allows evaluating the regenerative potential of the connective tissue. It is known that regeneration of connective tissue in an adult organism occurs due to the function of the stem/progenitor stromal cells that originate from differentiating/differentiated cells. Such progenitor stromal cells found in the connective tissue are determinative for the regenerative potential of the connective tissue, i.e., the ability of a tissue cell population to fully recover its structural components rather than to lose the components (as a result of ageing or damages of various genesis). Thus, the regenerative potential can be interpreted as a parameter which characterizes the principal ability of a cell population to tissue regeneration not considering the rate of the regenerative processes.

Due to it, the second important parameter for a general characterization of the efficacy of regenerative processes in connective tissues is the proliferative potential, i.e., the numbers of cell mitoses which could occur prior to cell death, i.e., it is the ability of the cells to multiple fissions to preserve a functionally active cell population in tissue. It is clear that the higher is the regenerative and proliferative potentials of the cells forming a tissue or organ, the larger is the number of the mitotically active cells, and, consequently, the quicker are regenerative processes.

Thus, both above-mentioned parameters, i.e., the regenerative potential (the presence and the number of "active" regeneration centers) and the proliferative potential (kinetic particularities of regenerative processes) supplement each other and define the tissue regeneration efficacy (the ability of tissue to regenerate). Thus, reduction or loss of a function of an organ/tissue could be considered from the point of view of abnormal regeneration, wherein regenerative and/or proliferative potentials are reduced. The detection of such types of abnormalities boils down to the determination and interpretation these parameters.

The present invention expands a range of modern methods for evaluation of connective tissues (and/or organs) and for detection of pathologies by introducing a simple, available and reliable methods to a general clinical practice which is based on clonal analysis of the substrate-dependent cells forming tissues.

This goal has been achieved by the present inventors who have developed universal diagnostic methods for live tissues and organs on the basis of cell population analysis (mesenchymal stromal cells, fibroblasts). Values of the regenerative and proliferative potentials which are obtained during testing can be used for diagnostic and/or prognostic purposes in dermatology (for example, for dermal examination with aging changes), dentistry (for example, paradontosis), and for diseases of the musculoskeletal system (for example, in chronic osteomyelitis, necrosis of femoral head, etc).

Thus, when the present invention is used for the evaluation of patient's skin status, such values allow making conclusions about morphofunctional status of a dermal fibroblast population and design an individual correction program for current skin changes and aging prophylaxis. Such a program can include recommendations concerning the number of cell therapy procedures (in particular, an intradermal injections of cultured autologous fibroblasts), their terms and also cosmetic methods applied in regard to their exposure of all of the skin layers to achieve stable aesthetic results without damaging the fibroblast population.

It is well-known fact that progenitor stromal cells being substrate-dependent cells, form discrete colonies in culture in vitro, each of which presents a generation of one cell (clone). Thus, when one performs clonal analysis and defines, for example, the efficacy of the colony formation (ECF), which presents a ratio of the grown fibroblast colonies to the number of cultured (explanted) cells, one could define the content of the progenitor cells in a sample of such tissue or organ. ECF is the value which reflects a proportion of the colony-forming (clonogenic) substrate-dependent cells in cell culture, and when recalculated in respect of the mass of a biopsy material, it shows the content of progenitor cells in the tissue. The higher is the efficacy of the colony formation, the larger is the content of the progenitor cells in the tissue, and, respectively, the larger is the number of the differentiating (mature) functionally active fibroblasts, and, consequently, the higher is the regenerative tissue potential, and vice versa.

The present inventors have studied and shown that when one uses special standardized conditions, results obtained for the colony formation are highly reproducible (with 5-7% bias) in regard to the number of formed colonies, shape and morphological properties of all cells of the tissue or organs with similar functions and location. It allows extrapolation of data concerning colonies and forming cells to the entire cell population, tissue and/organ and evaluation of their status and development of correction recommendations, when disorders of any type are observed.

Thus, a study of the colony forming effectiveness of the fibroblasts (CFE-f) is the most informative and precise method for the determination of the regenerative potential of a mesehchymal stromal cell population and, consequently, a test tissue.

A method of diagnosis of skin and/or organ status suggests conducting two stages of experiments:

1. Stage of preliminary studies. At this stage, parameters of connective tissue are defined which determine the regenerative and proliferative potentials of the substrate-dependent cells. The parameters should be defined at strictly controlled conditions on a large sample of donors with already known study results which confirm lack of abnormalities. As a result of the studies, the inventors have obtained a range of mean values for the parameters which define the regenerative and proliferative potentials of forming substrate-dependent cells which comply with the normal status of the tissue.
2. Stage of diagnosis. At this stage, the same parameters, as at the stage of preliminary studies, are defined which characterize the regenerative and proliferative potentials of the forming cells. However, at this stage, a patient whose status of the tested tissue (and/or organ) is being assessed, is tested. When the values of the parameters are obtained, they are compared with a pre-specified range of the mean values, which allows making a conclusion in regard to the absence of abnormalities.
    It should be noted that the stage of preliminary studies is not always required, as a range of the mean parameter values may be known from literature or other reliable sources.

The stage of diagnosis includes:
I. Cultivation of substrate-dependent cell colonies from the analyzed tissue (and/or organ) eligible for visualization. To achieve this step, the following procedures can be performed:
1. Obtaining a biopsy of a patient's tissue sample;
2. Isolating viable substrate-dependent cells from the tissue sample at the standard conditions;
3. Explantation of the isolated cells on the surface of cultural plastic with classic methods of cell culture and density which allows obtaining colonies for a statistically reliable analysis;
4. Cultivating the cells at the standard conditions for a controlled period of time which is sufficient for formation of discrete colonies eligible for visualization.
II. Statistically reliable analysis of the derived colonies.
The following steps could be performed:
1. Visualization of the formed colonies with standard means and protocols;
2. Analysis of colony images to obtain a range of parameters which characterize growth and morphological particularities of cell cultures which are subsequently used for the determination of the proliferative and regenerative potentials.
III. Processing the results.
Detailed Description of the Process Stage:
I. Cultivation of Substrate-Dependent Cell Colonies.
1. Tissue Sampling (Biopsy Material).
Biopsy of connective tissue is performed in aseptic conditions from an organ which is tested as a part of the present invention. The location and method of biopsy should be strictly standardized within one group of analyses. A site for the tissue biopsy is selected based on the provision of a representative sample of a tissue material which maximally reflects status of the concerned tissue (organ) not affected by the environmental factors.
2. Isolation of Viable Substrate-Dependent Cells.
Viable cells from the biopsy material of the patient's tissue are isolated at the sterile conditions according to standard protocols with proteolytic enzymes—collagenase or liberase. A goal of this stage is to release viable cells from the intercellular tissue matrix with the enzymatic degradation of the latter.
3. Cell Explanation.
A well-known and reproducible density of cell explanation is one of the important conditions for successful implementation of the embodiments of the present invention. Density of cell explanation depends on several factors including a type of cells and the number of passages in vitro, a composition of a culture medium, culture conditions and terms, an explanation area, substrate nature, etc. should be experimentally defined prior the routine use (at the stage of preliminary studies), based on the following:
The optimal density of cell explanation is considered as a density which contributes to the colony formation which size and number of the forming substrate-dependent cells allow making a statistically reliable analysis. Thus, the number of colonies should not be too large to prevent contact inhibition of the cells within a colony and their mitosis, which can result in a complicated interpretation of the results. For example, the optimal density of explanation for dermal fibroblasts is 1-2 cells/cm$^2$.
The number of explanted cells is precisely calculated with standard methods which can be used without limitations as a part of the invention.
Selection of appropriate passage of the explanted cells is made according to a specific goal, wherein studies on both primary cell cultures (if a test of patient's skin fibroblasts is performed), and later cell passages (if a cell product is characterized by prior therapy) should be carried out. Optimal conditions for each of the variants are individually selected in control tests.

It should be noted that one should use explanation and cell culture protocols which are identical to protocols specified at the stage of preliminary studies including culture conditions and set of reagents/materials, to obtain reliable and reproducible results. The latter is not always technically feasible for a long period of time, for example due to inevitable consumption of reagents from one batch. Thus, to provide a fuller control over specified conditions, the present invention has introduced "internal cell standards", i.e., the use of cell culture with previously determined parameters which define the regenerative and proliferative cell potentials. The "internal cell standard" had the same processing and analysis stages as the cells from the analyzed tissue sample. Then the present inventors compared parameter values for the internal cell standard with expected, pre-specified analogous values, and if the discrepancy is more than 10%, an adjusting factor is calculated which considers altered analysis conditions compared to the standard conditions. After that, specific parameters of the studied cells are calculated with regards to the adjusting factor.

4. Cultivation of the Cells.

The approach for determining the optimal duration of this stage with regards to culture conditions and a type of the used cells is analogous to that described above. Thus, the determination of the optimal time for cell incubation in a culture medium and standardization of the conditions is one of the important factors of achieving reproducible and statistically reliable results.

II. Statistically Reliable Colony Analysis

1. Colony Visualization.

A goal of this stage is to obtain an image of the formed colonies in such a form which is convenient for analysis, including those which are obtained with hardware and morphometric software. Resolution of the image, its format and image acquisition tools are chosen based on specific goals and parameters which characterize cell culture (see below). Domestic and professional scanning devices, digital photo- and video equipment, optical and electronic microscopy, etc., which are used to obtain electronic high-definition images of the colonies with resolution not less 800 dpi can be illustrative.

2. Analysis of Cell Colonies for the Quantitative Assessment of the Parameters which Characterize Cell Culture.

A goal of the present stage is to evaluate objective qualitative/semi-qualitative parameters which characterize properties of cell culture in respect to morphological signs of the formed colonies and cells forming the colonies. Such parameters include:

the total number of formed colonies. According to current practice [1,2], one should characterize the minimal number of the cells forming a colony which may include from 20 to 50 cells, preferably from 20 to 30 cells, and more preferably form 20 to 40 cells. The clones which include the smaller number of cells, are not considered as colonies and are not included in calculations.

efficacy of colony formation. This parameter characterizes the ability of the substrate-dependent cells to form colonies and represents a ratio of the grown colonies to the total number of the explanted cells.

any parameter which describes a form and size of colonies. In particular, such parameter includes a total area of all colonies, the mean area of the colonies, their linear size, the total or mean colony perimeter, their distribution per size, a proportion of the colonies which size lies within a certain range, etc. For example, if arbitrary critical values are introduced for the linear size of colonies, the colonies can be divided to "large", "moderate", and "small" colonies, and the proportion of each type of the colonies, their ratio, etc., could be calculated.

any parameter which characterizes structural and morphological characteristics of colonies. Such parameters include:

distribution of the colonies per the number of forming cells or density of cell localization in a colony. For example, when arbitrary mean values are introduced for the number of cells forming a colony, the colonies can be divided into "dense", "diffuse", "mixed", and the proportions of the colonies with various density, their ratios, etc., can be calculated;

proportion of the colonies with the number of cells which lie within a specified interval;

distribution of the colonies within the shape of cells forming the colonies. For example, in fibroblast colonies, the following cells are differentiated: spindle (narrow long cells with a ratio of the long and short sides >5), velum (large well-spread cells ≥40 μm in size with a ratio of the long and short sides <3), etc. Thus, colonies which include more than 75% of spindle cells are defined as "spindle", colonies with more than 75% of spindle cells—"velum", and the intermediate variants—"mixed" colonies;

it is also possible to use any combination of the above-mentioned methods, and also derive values obtained on the basis of the above-mentioned parameters.

It should be noted that a combination of possible parameters is not limited with the list given above and can include any other parameters and their combinations which characterize form, size, number, location density, etc. of both colonies, and cells forming the colonies.

III. Processing of Results.

This stage provides analysis of regenerative and proliferative potential values and their interpretation. It is appropriate to use mathematical methods which algorithms depend upon a test sample, a goal of the study and parameters which are obtained with clonal analysis. Values characterizing the colonies could be compared with the control (mean) values stored in a database or a memory cell and be retrieved for the comparison.

A goal of the present stage is to evaluate parameters which characterize colonies of the test cells by comparing their values with the control (mean) values which were obtained on the stage of preliminary studies, and to make a conclusion concerning the status of a test cell population or tissue (organ).

Hardware for conducting statistical analysis and mathematical modeling for achieving objective, statistically reliable (i.e., level of significance $\alpha$ is less than 5% (0.05)) information could be used. The control (mean) values are qualitatively determined on the basis of data which are obtained on the stage of preliminary studies, literature data and/or information from other reliable sources.

To use the invention simply and successfully, one could use a specially developed computer system (CS). The computer system for diagnosing includes an image forming unit which provides optical resolution of not less than 800 dpi, preferably and up to 9600 dpi, and more preferably 1200-1800 dpi, a central processing unit which is connected to a working memory unit and programmed to process information that is obtained directly from the image forming unit and/or information input/output unit. The computer system is provided with software for statistically reliable analysis of colonies, for the determination of at least one parameter which characterizes the regenerative potential and at least one parameter which characterizes the proliferative potential, and for processing the results, which allows evaluation of the regenerative potential of patient's tissue (or organ) by comparing the obtained values with the mean (normal) values stored in a database or a memory cell and retrieved for the comparison following by displaying or showing the diagnosis to a user, e.g., a doctor, patient, esthetician, etc.

The system can include (FIG. 1) a central processing unit (CPU, 1), which is connected with a working memory unit (WMU, 2) and can be programmed to process information that is obtained directly from an image forming unit (IFU, 3), and/or an information input/output unit (IOU, 4). Parameters which are obtained as a result of the information processing, are compared to the standard (normal) values that are kept in a database of a read-only memory unit (5) or other memory cell type of the computer system. IFU is used to obtain digital images of the formed cell colonies in the format that is eligible for its subsequent processing by a CS with resolution of not less than 800 dpi that provides visualization of the individual stained cells forming colonies. A such unit can function on the base of electronic flat-bed scanning devices, a digital photo or video camera and other digital image forming units which provide relevant resolution.

VARIANTS FOR APPLICATION OF THE INVENTION

In particular, the present diagnostic methods can be used for evaluation of dermal status.

One of the major tasks of modern dermatology and cosmetology is to solve a problem of effective and safe correction of age-related changes in the skin. At present, esthetic medicine uses a broad arsenal of methods for correction of age-related skin changes of the face and body, e.g., mesotherapy, biorevitalization, peeling, fractional photothermolysis, radio wave exposure, dermabrasion and other methods. The main goal of these methods is to stimulate functional activity of fibroblasts—the major cellular component of the dermis responsible for the production, organization, and renewal of its intercellular matrix.

The major causes of the skin aging are the decreased content of fibroblasts and reduction of their biosynthetic activity. A targeted action on the cellular level promotes both remodeling of the intercellular matrix and effective correction of visual defects of the skin.

The use of modern cosmetological procedures and methods for correcting wrinkles and other age-related defects of the skin shows that the methods are effective and safe only when individual peculiarities of the patient's skin are taken into account. Modern methods of assessing skin conditions, especially on the cellular level, are not sufficiently effective and have little practical significance.

The present inventors have solved the above discussed problems and have developed universal methods for examination of the skin of a patient which allows detection of various changes (e.g., age-related and structural changes) and expansion of diagnostic opportunities of the skin status with increased efficacy and safety of subsequent cosmetological procedures. In particular, the present inventors have developed methods for evaluating human dermal status.

In one embodiment, the method includes analysis of the parameters characterizing fibroblast colonies which includes the determination of the efficacy of colony formation as a parameter that defines the regenerative potential of a cell population and percentage of dense and diffuse colonies in cell culture, as a parameter that defines the proliferative cell potential.

When the efficacy of colony formation is less than 45% for men and 36% for women, the regenerative potential is diagnosed as being low. When the efficacy of colony formation is in the range of 45-49% for men and 36-45% for women, the regenerative potential is diagnosed as being normal. When the efficacy of colony formation is more than 49% for men and 45% for women, the regenerative potential is diagnosed as being high. When the percentage of dense colonies is less than 44%, and the percentage of diffuse colonies is more than 25% for men, and the percentage of dense colonies is less than 40%, and the percentage of diffuse colonies is more than 40% for women, the proliferative potential is diagnosed as being low. When the percentage of dense colonies is in the range 44-54%, and percentage of diffuse colonies is in the range 20-25% for men, and percentage of dence colonies is in the range of 40-50%, percentage of diffuse colonies is in the range of 30-40% for women, the proliferative potential is diagnosed as being normal. When the percentage of dense colonies is more than 54%, and the percentage of diffuse colonies is less than 20% for men, and the percentage of dense colonies is more than 50%, and the proportion of diffuse colonies is less than 30% for women, the proliferative potential is diagnosed as being high.

The efficacy of colony formation is calculated as the percentage of the formed colonies with the number of cells >20 to the total number of explanted cells.

To obtain objective, statistically significant information (i.e. α<0.05), parameter values which characterize fibroblast colonies, are defined with hardware tools and mathematic modeling according to the methods described below.

In another embodiment, the method includes analysis of the parameters characterizing fibroblast colonies which includes the determination of the efficacy of colony formation as the parameter that defines the regenerative potential of a cell population and the percentage of dense, diffuse, and mixed colonies in cell culture, and the proliferation index as the parameter which defines the proliferative cell potential. When the efficacy of colony formation is less than 45% for men and less than 36% for women, the regenerative potential is diagnosed as being low. When the efficacy of colony formation is in the range of 45-49% for men and 36-45% for women, the regenerative potential is diagnosed as being normal. When the efficacy of colony formation is more than 49% for men and more than 45% for women, the regenerative potential is diagnosed as being high. When the proliferative index is less than 2.0 for men and less than 1.8 for women, the proliferative potential is diagnosed as being low. When the proliferation index is in the range of 2.0-2.4 for men and 1.8-2.0 for women, the proliferative potential is diagnosed as being normal. When the proliferation index is more than 2.4 for men and more than 2.0 for women, the proliferative potential is diagnosed as being high.

The efficacy of colony formation is calculated as the percentage of the formed colonies with the number of cells >20 to the total number of explanted cells.

The proliferation index is defined by the following formula:

$$PI=[1(PD)+2(PM)+3(PS)]/100\%,$$

wherein
  PI is the Proliferation index;
  PD is the percentage of the diffuse colonies, (%);
  PM is the percentage of the mixed colonies, (%); and
  PS is the percentage of the dense colonies, (%).

In one embodiment, to obtain objective, statistically reliable information, parameter values which characterize fibroblast colonies, a computer system and statistical analysis and mathematical modeling are used. In this case a method for diagnosis of a condition of the skin of a patient comprises:
  assessing via a processor programmed to assess at least one parameter characterizing a colony of fibroblast cells of the skin of the patient, wherein the processor is programmed to execute the following:
  determining: (i) effectiveness of colony formation as a parameter characterizing a regenerative potential of the fibroblast cells of the patient and (ii) a proportion of dense colonies and a proportion of diffuse colonies in a culture of the fibroblast cells as a parameter characterizing a proliferative potential of the fibroblast cells of the patient,
  storing in memory the determined parameters (i) and (ii) and mean values of effectiveness of colony formation and a proportion of dense and diffuse colonies for a population in a database or a memory cell and retrieving the determined parameters and the mean values for a comparison, recalling the stored parameters and mean values form the memory, comparing via the processor the effectiveness of colony formation and the proportion of dense colonies and the proportion of diffuse colonies determined for the patient to mean values of effectiveness of colony formation and a proportion of dense and diffuse colonies for a population, and determining via the processor: (a) whether the regenerative potential of the patient is low, normal or high compared to the mean value of the regenerative potential of a population, and (b) whether the proliferative potential of the patient is low, normal or high compared to the mean value of the proliferative potential of a population, thereby providing a diagnosis of the condition of the skin of the patient.

Making a Conclusion and Recommendations

Values of the regenerative and proliferative potential allow making conclusions in regard to the functional status of a dermal fibroblast population and entire dermal of each patient and elaborating on an individual program for correction of aging skin changes.

The program includes recommendations concerning the number of cell therapy procedures with intradermal injections of cultured autologous skin fibroblasts, their terms and cosmetological methods applied in regards to their dermal exposure without any damage.

In particular, when the high regenerative (for men—more 49%, for women—45%) and proliferative (PI for men—more than 2.4 and for women—more than 2.0) potentials are determined, recommended cosmetological dermal methods are the methods that stimulate the proliferative activity of a skin fibroblast population, including the aggressive methods (e.g., laser ablative technologies).

When a patient has the normal regenerative (for men—45-49%, for women—36-45%) and proliferative (PI for men—2.0-2.4 and for women—1.8-2.0) potentials, a course of dermal autofibroblasts is recommended for the skin areas which require correction, as frequent as once in five years (as it is known that the synthetic activity of transplanted fibroblasts remains for at least 12 months), cosmetic procedures also have no limitations.

When a patient has low values of the regenerative (for men—less than 45%, for women—less than 36%) and proliferative (PI for men—less than 2.0 and for women—less than 1.8) potentials, a course of dermal autofibroblasts is recommended for the skin areas that require correction, as frequent as once in three years, and aggressive dermal methods should be used with caution. Thus, the higher are the abnormal values of the regenerative and proliferative potentials, the more often therapy courses with dermal autofibroblasts should be performed, up to once a year, when the regenerative potential for men is less than 25% and for women—less than 20%, and when the proliferative potential PI for men is less than 1.6 and for women—less than 1.5.

Having generally described this invention, a further understanding can be obtained by reference to certain specific examples which are provided herein for purposes of illustration only and are not intended to be limiting unless otherwise specified.

Example 1

Stage of Preliminary Studies

To analyze a patient's skin dermal fibroblast population, mean parameter values are specified for patient's dermal fibroblast colonies.

A group of 50 patients (35 women, 15 men) with signs of aging facial skin changes (wrinkles, decreased skin firmness) was enrolled into the study.

The facial skin of a patient was studied to determine such characteristics as skin texture, depth of the wrinkles, and a level of microcirculation, that was carried out with the following instrumental methods for skin studies:

study of skin hemocirculation with laser Doppler flowmetry (laser blood flow analyzer LAKK-01, NPO "Lazma", Russia);

study of mechanic skin characteristics with a vacuum cutometer (CUTOMETER® MPA 580, Courage+ Khazaka electronic GmbH, Germany);

general study of microrelief and visual skin values with a photometric system (VISTA®, Proctor&Gamble Co, USA).

After the skin had been examined with the instrumental methods, parameters characterizing dermal fibroblast colonies were determined. For that, a biopsy and cell culture were prepared.

All of the procedures were carried out in accordance with the medical technology approved by the Roszdravnadzor RF "Sampling, shipment, isolation, culture, cryopreservation, storage and use of autologous fibroblasts for correction of aging and cicatrical skin changes" (FS approval No. 2009/398).

A the skin biopsy of 3-5 mm$^3$ in size was obtained with a disposable surgical blade from behind the ear auricle under local infiltrative anesthesia with a 2% lidocaine solution if patients did not have any contraindications. The isolated skin fragment was immediately transferred to a labeled sterile container with a shipment medium (DMEM/F12).

After the biomaterial was brought to a laboratory, it was transferred to a Petri dish at sterile conditions, washed with a Hank's solution and an antibiotic agent (gentamycin), and then with a Versene solution for three times. The material was dispersed with a sterile scalpel, a disaggregating 0.1% collagenase solution was added and the material was incubated for 1-1.5 hours in 37° C.

After the incubation, the tissue suspension was intensively pipetted and centrifuged for 10 minutes at 300 g, the supernatant was removed, the precipitate was diluted with a culture medium (DMEM/F 12 1:1) supplemented with 10% human umbilical blood serum (UBS) and 10% autologous serum (AS), or DMEM/F12 1:1 with the addition of 10% UBS and 10% bovine fetal serum (FBS) (SPA "PanEko", Russia) or FBS Defined (HYCLONE® Laboratory, Inc., USA) or DMEM/F12 1:1 with the addition of 20% FBS (SPA "PanEko", Russia) or FBS Defined produced by HYCLONE® Laboratory, Inc., USA and 40 µg/ml of gentamycin, resuspended and transferred to a culture vial. The culture vial was transferred to a $CO_2$-incubator. The cells were cultured at +37° C. in the 5% $CO_2$ atmosphere. The cultural medium was changed every 3-4 days.

After reaching a subconfluent monolayer, the cells were washed with a Versene solution and removed from the surface of a cultural flask with a Versene solution and 0.25% trypsin, resuspended in a cultural medium and explanted in a larger cultural flask for subsequent culturing.

Subsequently, a clonal fibroblast analysis had been performed. When a second cell passage was achieved, the cell culture was washed for three times with a Versene solution and trypsinized at 37° C., 5% $CO_2$ for 10 min. The homogenate was centrifuged for 10 minutes at 300 g. The supernatant fluid was removed, cells were resuspended in a Hank's solution and counted in a Gorjaev's chamber up to when the resultant number was not less than 95%.

Serial dilutions were used to prepare a cell suspension having a concentration of 100 cells/ml. In three Petri dishes 100 mm in diameter, a cultural medium was transferred (DMEM/F12 1:1 with the addition of 10% UBS and 10% AS, or DMEM/F12 1:1 with the addition of 10% UBS and 10% FBS (SPA "PanEko", Russia) or FBS Defined (HYCLONE® Laboratory, Inc., USA), or DMEM/F12 1:1 with the addition of 20% bovine embryonic serum (SPA "PanEko", Russia) or FBS Defined (HYCLONE® Laboratory, Inc., USA), and 40 µg/ml of gentamycin) and explanted per 1 ml of the cell suspension to obtain a clonal inoculum density of 1.5 cells/$cm^2$.

The Petri dishes were incubated in a $CO_2$-incubator at the saturated humidity conditions at +37° C. in the 5% $CO_2$ atmosphere for 14 days. Thereafter, the culture dishes with the formed colonies were washed with a phosphate-buffer solution for three times (PH 7.2-7.4) and fixed with 70% alcohol at room temperature for 15 minutes. Then alcohol residuals were removed by triple washing with distilled water, and the colonies were stained with a KARYOMAX® Giemsa Stain Stock Solution produced by GIBCO® USA, for 20 minutes at 37° C. The dishes with the stained colonies were thoroughly washed from excessive colorant and dried at room temperature for 5-7 hours.

Thereafter, the morphometric analysis of the colonies was carried out with the determination of the mean optical density of each studied colony.

The culture dishes were transferred to a gel-documenting system CHEMDOC® XRS Universalhood II (BIORAD® Inc., USA), and their entire surface was scanned in a visible light range to obtain an electronic image of the colonies with resolution not less 800 dpi.

The electronic image of the colonies was processed with the morphometric program IMAGEJ® according to the algorithm which includes removal of excessive staining in a Petri dish, determining the boundaries of individual cell colonies, removal of image artifacts which distort calculation, and colony analysis, and calculation of the mean (per colony area) optic density for each studied colony (FIG. 1B).

The counting of the colonies was carried out as described below.

After the morphometric analysis, the obtained data for the mean optical density were imported into the MICROSOFT® EXEL program, wherein the overall counting of the colonies was performed. All of the colonies were ranked according to their mean optical density (MOD) in three groups: dense colonies (MOD≥46 rel. units), diffuse colonies (MOD≤25 rel. units) and mixed colonies (25<MOD<46 rel. units).

These colonies were characterized based on the following parameters:

The colony forming effectiveness of the fibroblasts (CFE-f) was determined, which characterizes the content of the fibroblast precursor cells in the patient's skin and serves as a quantitative index of the regenerative potential of a population of dermal fibroblasts of a patient. CFE-f is a ratio of the formed colonies which include more than 20 cells to the total number of explanted cells. The clones of fibroblasts which include fewer cells were not considered as colonies and, accordingly, were not included in the count.

The linear dimension of a colony, which is characterized by a diameter of the circle (in µm) including the entire colony, was determined by using a standard operation of the IMAGEJ® program.

The mean area of the colonies, which is the area distribution over the number of the colonies, was determined by using a standard operation of the IMAGEJ® program.

The number of dense colonies and the proportion of all colonies formed with more than 20 cells were determined.

The number of diffuse colonies and the proportion of all colonies formed with more than 20 cells were determined.

The number of mixed colonies and the proportion of all colonies formed with more than 20 cells were determined.

The mean optical density of the colonies, which was determined by using a standard operation of the IMAGEJ® program, and its distribution over the dense, diffuse and mixed colonies were determined.

The mean optical density of the dense colonies, which is proportional to the number of cells included in the colony, was determined by using a standard operation of the IMAGEJ® program.

The proliferation index, PI, is defined by [See, Vladimirskaya Ye. B., Koshel' I. V., Tsurya V. M. et al. "Stromal fibroblasts of normal bone marrow in children", *Gematologiya* No. 1, 1990, pp. 1-4]:

$$PI=[1(PD)+2(PM)+3(PS)]/100\%,$$

wherein
PI is the Proliferation Index;
PD is the proportion of the diffuse colonies, (%),
PM is the proportion of the mixed colonies, (%), and
PS is the proportion of the dense colonies, (%).

The obtained parameters of cell colonies, which characterize a population of the dermal fibroblasts of a patient, were compared to the parameters of the instrumental analysis of the skin of the patient by using the statistical program BIOSTAT® and a correlation analysis for determining the mean values of the parameters (a level of statistical significance is $\alpha<0.05$).

After establishing stable, statistically reliable correlation between the characteristics of the colonies of dermal fibroblasts and the characteristics of the skin condition obtained by the instrumental methods of the skin analysis by applying methods of mathematical statistics, the mean values of the most statistically significant parameters of a population were determined (with the Pearson correlation factor greater than 0.7), e.g., the colony forming effectiveness of the dermal fibroblasts (%), the percentage of the dense colonies (%), the percentage of the diffuse colonies (%), and the proliferation index.

To obtain objective, statistically significant information, computer technology, statistical analysis, and mathematical modeling were applied.

Figure 3:
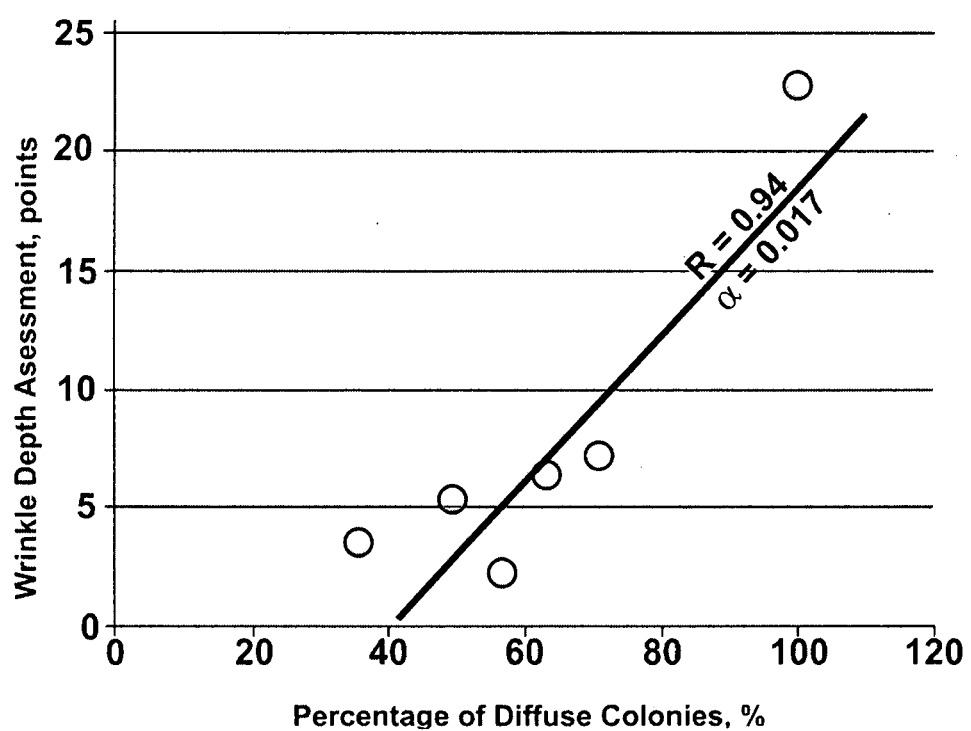
FIG. 3-5. Results of clonal analysis. Diagrams of the statistically significant dependencies which are observed with the Pearson correlation analysis, where R is a Pearson correlation coefficient (the closer to 1, the stronger is the dependence of the test parameters) with a statistical significance level $\alpha$.
Figure 4:
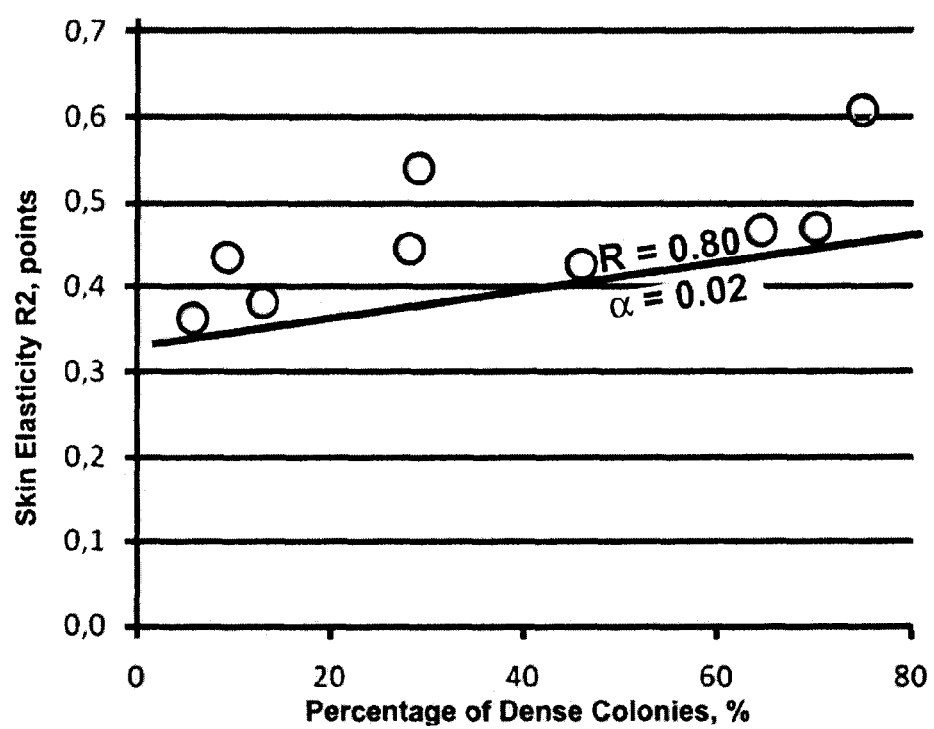
Figure 5:
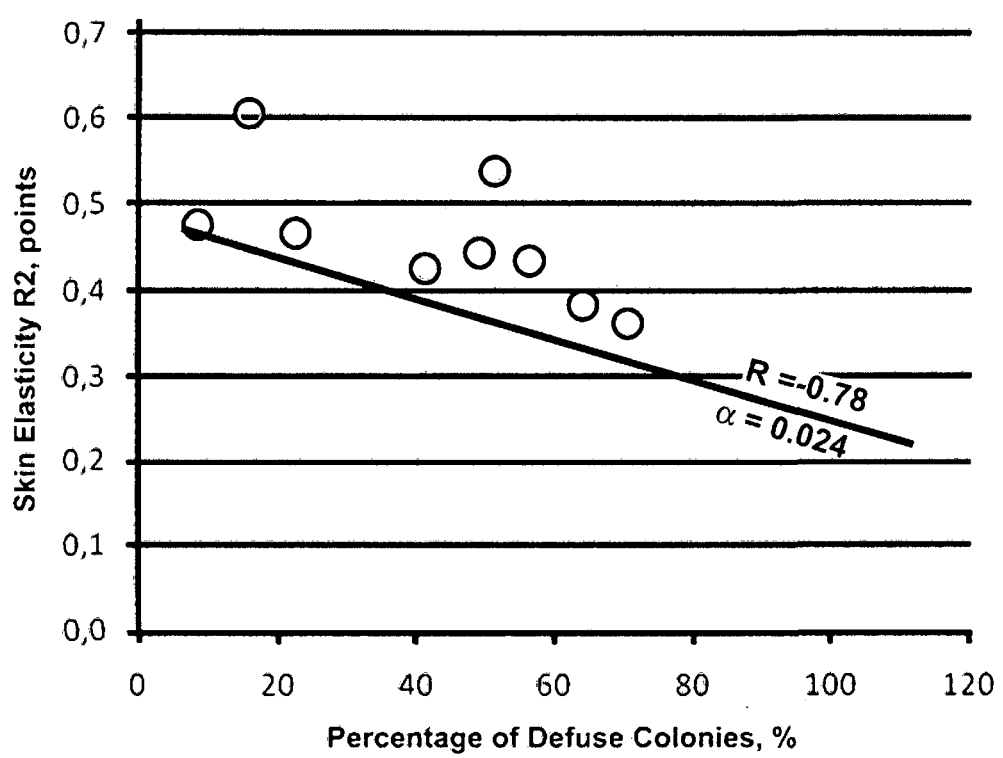

The results of the clonal analysis are presented on FIG. 3, FIG. 4 and FIG. 5, wherein the parameter dependency diagrams were determined by using Pearson correlation analysis.

Table 1 shows mean values of the abovementioned significant parameters of the dermal fibroblasts depending on the sex of the patient.

TABLE 1

| Parameter | Mean parameter value | |
|---|---|---|
| | Men | Woman |
| Efficacy of colony formation, % | 45-49 | 36-45 |
| Proportion of dense colonies, % | 44-54 | 40-50 |
| Proportion of diffuse colonies, % | 20-25 | 30-40 |
| Proliferation index | 2.0-2.4 | 1.8-2.0 |

The parameter values are relative and applicable for the comparison and analysis of the cells which are derived at the strictly controlled conditions, such as a standard composition of a cultural medium and culture conditions.

When the combinations of PD and PS values do not allow making an unambiguous conclusion about significance of the proliferative potential (for example, for men: PD>25 and PS>54, or PD<20 and 44<PS<54, or PD<20 and PS<44; for women: PD>40 and PS>50, or 30<PD<40 and PS<40, or PD<30 и PS<40), the proliferation index is calculated (PI), which, owing to the contribution of all types of colonies of, allows making an unambiguous conclusion about significance of the cell culture.

Example 2

Female patient K came to clinic A concerning correction of aging skin changes (considerable skin thinning, numerous fine static wrinkles in all face zones). The patient was 56 years old and had been menopausal for 5 years. In the menopause, aging skin changes are significantly increased [Brincat M. Hormone replacement therapy and the skin. Maturitas.-2000.-V.35.-N2.-p. 107-117]. In order to select adequate therapy according to the patient's skin status, the regenerative and proliferative potentials of a dermal fibroblast population were evaluated. Specifically, the skin was taken from behind her ear, and clonal analysis was performed to define the parameters characterizing the dermal fibroblast colonies according to the abovementioned method.

Figure 6:
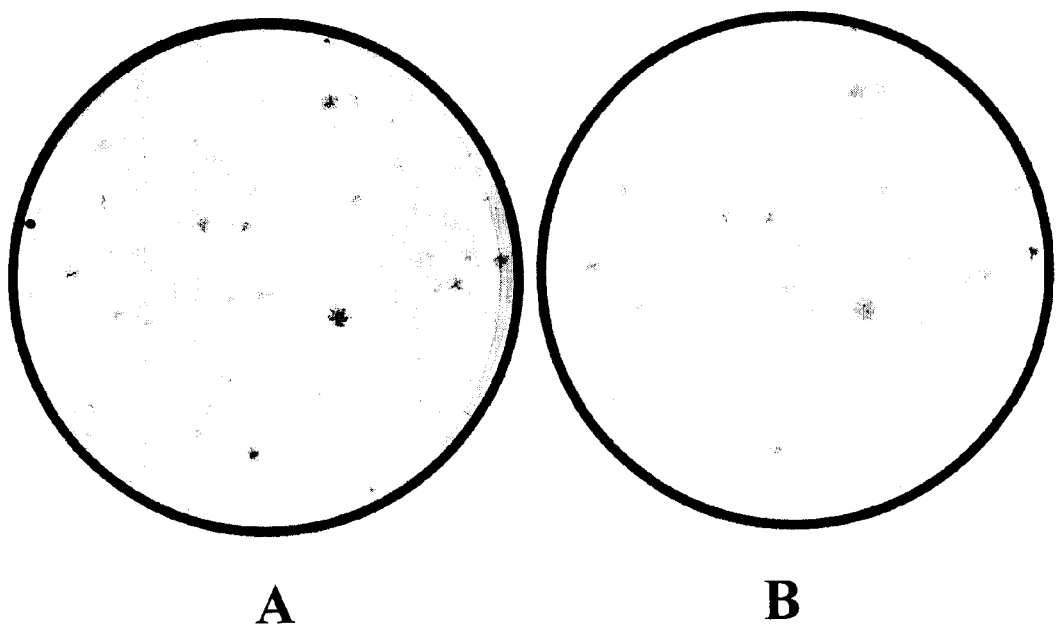
FIG. 6. An electronic image of the colonies (A) and the results of their computer processing for the morphometric analysis (B) (female patient K, 56 years).

The electronic colony imaging is presented in FIG. 6A, and the results of the computer processing for the morphometric analysis is presented in FIG. 6B.

The results of the measurement of the size and mean optical density of the colonies with the program IMAGEJ® are presented in Table 2.

TABLE 2

| Colony No | Colony area, [relative optical area unit] | Integral optical density of colonies, [relative optical density unit] | Mean optical density of colony | Type of colony (result of computer analysis) |
|---|---|---|---|---|
| 1 | 5494 | 242614 | 44.2 | Mixed |
| 2 | 4519 | 247278 | 54.7 | Dense |
| 3 | 4388 | 233256 | 53.2 | Dense |
| 4 | 4841 | 235662 | 48.7 | Dense |
| 5 | 5611 | 120398 | 21.5 | Diffuse |
| 6 | 4599 | 105235 | 22.9 | Diffuse |
| 7 | 9000 | 133398 | 14.8 | Diffuse |
| 8 | 17902 | 325727 | 18.2 | Diffuse |
| 9 | 23068 | 466340 | 20.2 | Diffuse |
| 10 | 27136 | 493624 | 18.2 | Diffuse |
| 11 | 8496 | 130229 | 15.3 | Diffuse |
| 12 | 6285 | 149714 | 23.8 | Diffuse |
| 13 | 10026 | 192911 | 19.2 | Diffuse |
| 14 | 21193 | 429798 | 20.3 | Diffuse |
| 15 | 28759 | 381305 | 13.3 | Diffuse |
| 16 | 3230 | 167485 | 51.9 | Dense |
| 17 | 8949 | 118966 | 13.3 | Diffuse |
| 18 | 8492 | 165474 | 19.5 | Diffuse |
| 19 | 25656 | 324053 | 12.6 | Diffuse |
| 20 | 43501 | 502749 | 11.6 | Diffuse |
| 21 | 3510 | 179474 | 51.1 | Dense |
| 22 | 11148 | 712587 | 63.9 | Dense |
| 23 | 4323 | 244007 | 56.4 | Dense |
| 24 | 10415 | 196291 | 18.8 | Diffuse |

The following values were obtained:

[CFE-f]=24/1.5=16.0%, wherein 24 is the number of the formed colonies from 150 cultured cells, and 1.5 is a conversion ratio for calculating % of clonogenic cells relative to the number of cultured cells (150 cells/plate).

The proportion of dense colonies was determined as follows:

[PS]=7×100%/24=29.2%, wherein 7 is the number of the dense colonies; and 24 is the total number of colonies.

The proportion of diffuse colonies was determined as follows:

[PD]=16×100%/24=66.6%, wherein 16 is the number of the diffuse colonies; and 24 is the total number of colonies.

The comparison of the obtained data which characterize colonies, with the previously calculated mean values (Table 1) allowed making the following conclusions concerning the status of the skin fibroblast population of the female patient:

CFE-f was significantly lower than the average level which showed that the regenerative potential of the female patient's skin fibroblasts was low.

The proportion of the dense colonies was lower, and the proportion of the diffuse colonies was higher than the normal value which showed that the proliferative potential of the female patient's skin fibroblasts was low.

Based on these results, an individual program for correction of aging facial changes was recommended to female patient K which includes: a therapy course of autologous dermal fibroblasts, then in 8-12 months—a superficial peeling or fractional photothermolysis (in the papillary layer, not more than 3 procedures) and in 6 months—a secondary course of skin therapy with autologous dermal fibroblasts. As a result of the treatment, a considerable increase of the skin thickness was observed, in particular, in the paraorbital area, and also increase of skin elasticity and firmness, and reduction of the wrinkle number and depth.

Example 3

Female patient G applied to a clinic concerning significant skin thinning in the paraorbital area after secondary blepharoplasty. A visual examination had revealed thinning of the skin in the paraorbital area, reducing turgor, and the presence of multiple fine wrinkles. To select adequate therapy for the patient's skin, the regenerative and proliferative potentials of her dermal fibroblasts were evaluated. For that, skin was taken from behind her ear, and clonal analysis was performed to determine the parameters which characterize colonies of dermal fibroblasts according to the abovementioned method.

The parameters which characterized patient's skin fibroblast colonies were obtained with the abovementioned method:

CFE-f—8.3%;

[PS]—19%; and

[PD]—59%.

Conclusions:

CFE-f was significantly lower than the average level which showed that the low regenerative potential of the female patient's skin fibroblasts.

The proportion of dense colonies was lower, and the proportion of diffuse colonies was higher than the normal value which showed the low proliferative potential of the female patient's skin fibroblasts.

Based on the results, the female patient was recommended two courses of skin therapy with autologous dermal fibroblasts. After the therapy in the paraorbital area, the skin thickness, its elasticity and firmness were increased, and the number and deepness of the wrinkles were reduced. The patient was recommended to repeat the cell therapy in 3 years for preventive purposes.

Example 4

Patient N applied to clinic A concerning correction of aging skin changes (expression lines in the lip area, reduced skin turgor).

The parameters which characterized patient's skin fibroblast colonies were obtained with the abovementioned method:

CFE-f—60%;
[PS]—24%;
[PD]—46%.

Conclusions:

CFE-f was higher than the average level which showed that the regenerative potential of the patient's skin fibroblasts was high.

The proportions of dense colonies and diffuse colonies were in the normal value range which showed that the proliferative potential of the female patient's skin fibroblasts was normal.

Based on the results, any aesthetic procedures available in the clinic were recommended to the patient to correct aging skin changes without limitations according to the instruction.

Example 5

Female patient D applied to clinic A concerning wrinkle correction and flabbiness of the skin. The patient was a 36-year old woman with normal endocrine status, wherein the skin aggravation occurred after she had had a "THERMAGE®" procedure in one of the Moscow's clinics. To determine the reason of such skin changes, an examination of a patient's dermal fibroblast population was conducted. A sample of the skin was taken from behind her ear, and a clonal analysis was performed to determine the parameters which characterize dermal fibroblast colonies according to the abovementioned method.

Figure 7:
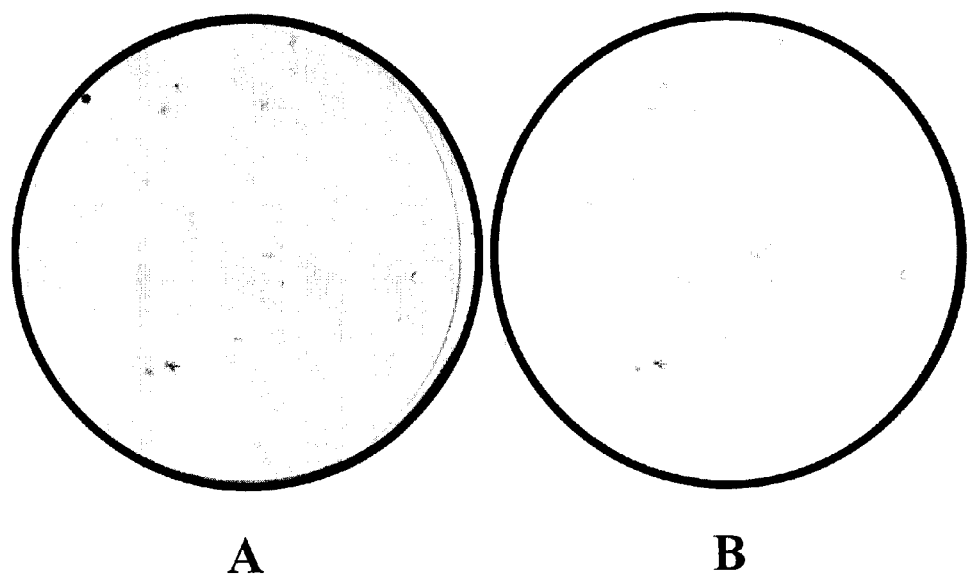
FIG. 7. An electronic image of the colonies (A) and the results of their computer processing for the morphometric analysis (B) (female patient D, 36 years).

The electronic image of the colonies is presented in FIG. 7A, and the results of their computer processing for the morphometric analysis is presented in FIG. 7B. The size and mean optical density which were calculated with the program IMAGEJ® are shown in Table 3.

TABLE 3

| Colony No | Colony area, [relative optical area unit] | Integral optical density of colonies, [relative optical density unit] | Mean optical density of colony | Type of colony (result of computer analysis) |
|---|---|---|---|---|
| 1 | 15215 | 299286 | 19.7 | Diffuse |
| 2 | 5695 | 97193 | 17.1 | Diffuse |
| 3 | 14526 | 98945 | 6.8 | Diffuse |
| 4 | 8654 | 103538 | 12.0 | Diffuse |
| 5 | 8524 | 109276 | 12.8 | Diffuse |
| 6 | 8967 | 159786 | 17.8 | Diffuse |
| 7 | 11949 | 142010 | 11.9 | Diffuse |
| 8 | 9429 | 69282 | 7.3 | Diffuse |
| 9 | 9618 | 49217 | 5.1 | Diffuse |
| 10 | 3942 | 159815 | 40.5 | Mixed |
| 11 | 4597 | 33656 | 7.3 | Diffuse |
| 12 | 11075 | 480888 | 43.4 | Mixed |
| 13 | 2267 | 24992 | 11.0 | Diffuse |
| 14 | 3609 | 44234 | 12.3 | Diffuse |
| 15 | 19830 | 1053603 | 53.1 | Dense |
| 16 | 12351 | 789057 | 63.9 | Dense |
| 17 | 20863 | 322777 | 15.5 | Diffuse |
| 18 | 8015 | 501089 | 62.5 | Dense |
| 19 | 8185 | 327993 | 40.1 | Mixed |
| 20 | 8050 | 355112 | 44.1 | Mixed |
| 21 | 1469 | 58104 | 39.6 | Mixed |
| 22 | 13037 | 154874 | 11.9 | Diffuse |
| 23 | 2326 | 83741 | 36.0 | Mixed |
| 24 | 6027 | 265022 | 44.0 | Mixed |
| 25 | 7617 | 61955 | 8.1 | Diffuse |
| 26 | 7151 | 54413 | 7.6 | Diffuse |
| 27 | 7145 | 337810 | 47.3 | Dense |
| 28 | 2895 | 48985 | 16.9 | Diffuse |
| 29 | 7674 | 336033 | 43.8 | Mixed |
| 30 | 1852 | 65829 | 35.5 | Mixed |
| 31 | 12802 | 525003 | 41.0 | Mixed |
| 32 | 15872 | 136871 | 8.6 | Diffuse |
| 33 | 4573 | 186589 | 40.8 | Mixed |
| 34 | 9434 | 404613 | 42.9 | Mixed |
| 35 | 8320 | 324331 | 39.0 | Mixed |
| 36 | 12326 | 247570 | 20.1 | Diffuse |
| 37 | 2250 | 101598 | 45.2 | Mixed |
| 38 | 3729 | 82953 | 22.2 | Diffuse |
| 39 | 14223 | 100829 | 7.1 | Diffuse |
| 40 | 3589 | 157622 | 43.9 | Mixed |
| 41 | 4412 | 119878 | 27.2 | Mixed |
| 42 | 4051 | 43444 | 10.7 | Diffuse |
| 43 | 8478 | 59390 | 7.0 | Diffuse |
| 44 | 4837 | 222351 | 46.0 | Mixed |
| 45 | 11869 | 60156 | 5.1 | Diffuse |
| 46 | 3739 | 230874 | 61.7 | Dense |
| 47 | 3900 | 99452 | 25.5 | Mixed |

The following values were obtained:

CFE-f=47/1.5=31.3%, wherein 47 is the number of the formed colonies from 150 cultured cells, and 1.5 is a conversion ratio for calculating % of clonogenic cells relative to the number of cultured cells (150 cells/plate).

The proportion of dense colonies was determined as follows:

[SC]=5×100%/47=11%, wherein 5 is the number of the dense colonies; and 47 is the total number of colonies.

The proportion of diffuse colonies was determined as follows:

[PD]=24×100%/47=51%, wherein 24 is the number of the diffuse colonies; and 47 is the total number of colonies.

The proportion of mixed colonies was determined as follows:

[PM]=18×100%/47=38%, wherein 18 is the number of the mixed colonies; and 47 is the total number of colonies.

The Proliferation index was determined as follows:

[PI]=(11×3+38×2+51×1)/100%=1.60.

The comparison of the obtained data which characterize cell colonies, with the previously calculated mean values (table 1) allowed making the following conclusions concerning the status of the skin fibroblast population of the female patient:

CFE-f was lower than the average level which showed that the regenerative potential of the female patient's skin fibroblasts was low.

[PI] was lower than the average level which showed that the proliferative potential of the female patient's skin fibroblasts was low.

Based on the results, two courses of skin cell therapy with autologous dermal fibroblasts were recommended to this female patient (with a 1-month interval). Already in one month after the therapy, increased skin elasticity, firmness and hydration were observed, as well as improved texture, and reduced number and depth of the wrinkles. The effect was progressive and had achieved the maximum intensity in 8 months after the therapy.

Example 6

Patient M came to clinic A concerning facial skin worsening after a course of photothermal thermolysis in one of the clinics with an apparatus PALOMAR® 1450 for correction of aging facial changes. After 3 procedures, skin turgor was decreased, numerous loci of dermal atrophy in the buccal area up 0.4 mm were observed, and the skin looked unhealthy. The parameters which characterized patient's skin fibroblast colonies were obtained:

EFC-f—10%; and
[PI]—1.49.

Conclusions:

CFE-f was significantly lower than the average level which showed that the regenerative potential of the patient's skin fibroblasts was low.

[PI] showed that the proliferative potential of the patient's skin fibroblasts was low.

Based on these results, two courses of skin cell therapy with autologous dermal fibroblasts were recommended to the patient. After the therapy, increased resilience and skin elasticity, improved color and contour of the face, and a significant decrease in the dimensions of dermal atrophy sites were observed. For preventive purposes, it was recommended to repeat the cell therapy course after 3-4 years.

Example 7

Female patient P applied to clinic A concerning correction of aging facial changes (eye wrinkles, marked nasolabial folds).

As a result of the parameter evaluation which characterized patient's skin fibroblast colonies, the following values were obtained:

EFC-f—36%;
PS—35%; and
PD—29%.

As it was not possible to draw a definitive conclusion as to the value of the proliferative potential of cell culture of this patient (as the proportion of the diffuse colonies DD was substantially below the mean value (30-40%) and the proportion of the dense colonies DP was less than the mean value (40-50%) for women), an additional measurement was carried out for the proportion of the mixed colonies DC, which was 36%, and the proliferation index PP of 2.06 was calculated.

Based on these results, the following conclusion was made about the status of the patient's skin fibroblasts:

CFE-f was almost equal to the average level which showed that the regenerative potential of the patient's skin fibroblasts was normal.

[PI] showed that the proliferative potential of the patient's skin fibroblasts was high.

Based on these results, an individual program for skin defect correction was developed which included fractional thermolysis of the entire face (according to the instruction), and in 6 months, a course of autologous dermal fibroblasts for wrinkle correction in the paraorbital area and nasolabial folds.

Thus, the present invention allows diagnosis of a population of fibroblasts of the patient's dermis by determining objective, quantitative parameters characterizing the regenerative and proliferative potentials of a population of fibroblasts.

The present invention produces unique results, which are useful for determining causes of complications provoked by the unmonitored uses of certain cosmetological methods, by evaluating the condition of a population of fibroblasts of the patient's skin. These methods may become indispensable in the prognosis of potential complications when using various cosmetological methods and procedures, and may also be a useful tool for doctors to understand processes which take place in the skin during certain complications, and for developing individual programs for correcting age-related skin changes for an individual patient.

Figure 8:
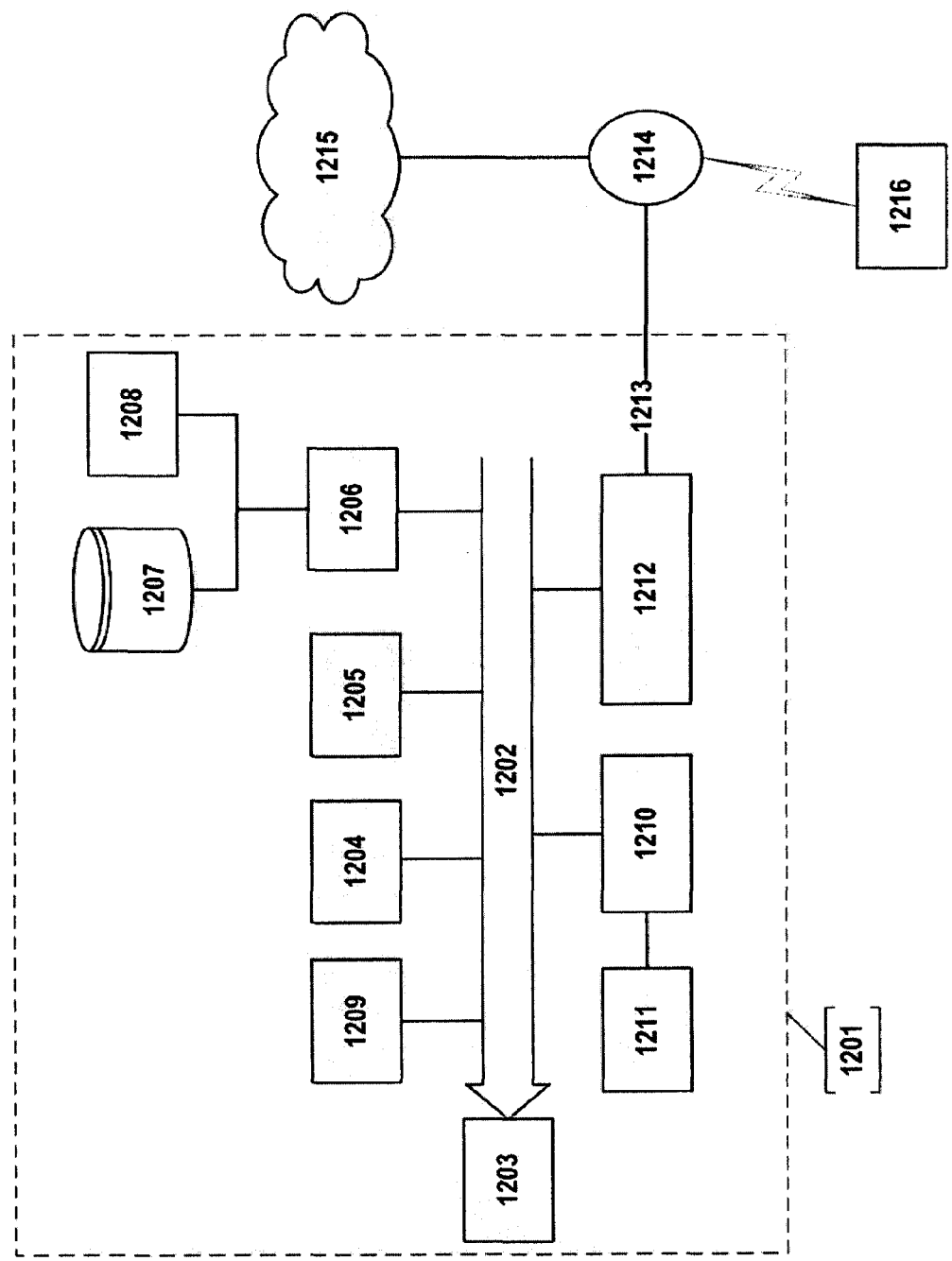
FIG. 8. Interaction scheme of the main functional blocks of a computer system.

If the abovementioned algorithm for cell colony analysis is used, considering complexity of the calculations and necessity to obtain objective parameters for evaluation of tissue (and organ) status, as a part of the invention, a computer system (CS) could be used to select, process and analyze information which is obtained in the analysis. To implement various diagnostic methods, computer systems with various specific configuration and programmed to execute specific steps can be used. The detailed scheme of a CS is presented on FIG. 8.

CS includes information channel 1202 (bus) or other mechanisms for information transfer and processor 1203 which is connected with a bus for information transfer. CS 1201 also includes basic memory unit 1204 based on random access memory units (RAM) or other dynamic assess memory units (for example, DRAM) or static random access memory units SRAM or synchronous dynamic access memory units SDRAM which are connected to bus 1202 to keep operational information and working instructions for central processing unit 1203. Besides, main memory unit can be used to keep temporary variables or temporary information for instruction execution by processing unit 1203. Then CS includes read-only memory unit (ROM) 1205 or fixed memory unit (for example, programmable read-only memory (PROM), erasable programmable read-only memory (EPROM) or electric erasable programmable read-only memory (EEPROM) which are connected with bus 1202 to keep permanent information and instructions for central processing unit 1203.

Besides, CS 1201 also includes hard disk controller 1206, connected with bus 1202 to control one or several storage devices to store a program and instructions for executing a method for determining the mean values. Such devices include magnetic hard disk 1207 and removable media 1208 (for example, floppy-disk drive, reading CD and DVD drive, writing/reading CD and DVD drive, magneto-optical disk drive, etc.). Storage devices can be also connected with CS 1201 through relevant interface (for example, interfaces SCSI, IDE, EIDE, SATA, eSATA), direct-access devices to DMA or ultra-DMA.

Thus, the basic memory unit 1204 and/or storage devices can be used for long-term storing of the mean (normal) values or for temporary storing of obtained values, and as a retrieving unit programmed to retrieve the mean values from the database or the memory cell and provide the mean values to the comparing unit.

Moreover, CS 1201 can also include specialized logical devices (for example, specialized integrated microcircuits (ASIC) or the simplest (SPLD), or complex (CPLD) programmed logical microcircuits or programmed logical matrix FPGA.

For closer integration of all functions of the proposed device, it can be also completed with image forming unit 1211 (IFU) which is managed by controller 1210. IFU 1211 can function on the base of any devices for digital image formation which provide optical resolution not less 800 dpi, more preferably—not less than 1200 dpi. Such devices can include electronic devices to read-out two-dimensional (flat) image and represent it in scanning electronic form (scanners), or digital devices based on charge transfer technology (CCD matrix—charge transfer device), for example, digital video and photo cameras. The main function of IFU 1211 is to obtain digital image of cell colonies which are derived in accordance with the description of the invention, and its digital transfer with controller 1210 and bus 1202 for further processing by processing unit 1203 and/or store in database on hard disk 1207.

CS 1201 can further include display controller 1209 which is connected to bus wire 1202 and used to control a display based, for example, on cathode-ray tube (CRT) or light-emitting diode (LED), to represent information to CS user. CS also includes input device, for example, keyboard and pointing device to interact with a user and report information to processing unit 1203. Pointing devices can include computer mouse, track-ball and stylus. Besides, CS can be completed with printing device to output an information or data which are kept and/or obtained as a result of actions by CS 1201.

CS 1201 performs calculation stages fully or partially which are provided with the invention if central processing unit 1203 receives and makes one or several instruction sequences which are contained in the memory, for example, main system memory 1204, to assess parameters characterizing at least one colony of fibroblast cells of the skin of the subject. Such instructions can be read out by main memory 1204 from another device, such as hard disk 1207 or removable storage device 1208.

Besides, processing unit 1203 also can comprise:
a first determining unit programmed to determine (i) effectiveness of colony formation as a parameter characterizing a regenerative potential of the cells of the subject, and (ii) a proportion of dense and diffuse colonies in a culture of the cells as a parameter characterizing a proliferative potential of the cells of the subject,
a comparing unit programmed to compare the effectiveness of colony formation and the proportion of dense and diffuse colonies determined for the subject to mean values of effectiveness of colony formation and a proportion of dense and diffuse colonies for a population, and
a second determining unit programmed to determine
  (a) whether the regenerative potential of the subject is low, normal or high compared to the mean value of the regenerative potential of a population, and
  (b) whether the proliferative potential of the patient is low, normal or high compared to the mean value of the proliferative potential of a population.

Also a computer system for providing diagnosis of a condition of the skin of a subject can comprises:

a programmed processor programmed to assess parameters characterizing at least one colony of fibroblast cells of the skin of the subject, wherein the programmed processor comprises: a first determining unit programmed to determine: (i) effectiveness of colony formation as a parameter characterizing a regenerative potential of the cells of the subject, and (ii) a proportion of dense and diffuse colonies in a culture of the cells as a parameter characterizing a proliferative potential of the cells of the subject,
a comparing unit programmed to compare the effectiveness of colony formation and the proportion of dense and diffuse colonies determined for the subject to mean values of effectiveness of colony formation and a proportion of dense and diffuse colonies for a population, and
a second determining unit programmed to determine: (a) whether the regenerative potential of the subject is low, normal or high compared to the mean value of the regenerative potential of a population, and (b) whether the proliferative potential of the patient is low, normal or high compared to the mean value of the proliferative potential of a population.

To process instruction sequences from main memory 1204, one or several processing units can be used in multi-processor CS configuration. According to another variant of the invention, instead or together with program instructions, it is also possible to make instructions transferred by wire communications. So, variants of implementation of the invention are not limited with any combination of apparatuses and software.

CS 1201 also includes communicative interface 1213 which is connected with bus 1202. The interface performs two-way data exchange via network connection 1214 which can be made, for example, with local area network (LAN) 1215 or another communication network 1216, for example, Internet.

Communication interface 1212 can be represented by network card to connect LAN with packet communication, by asymmetric digital subscriber line (ADSL) card, integrated services digital network (ISDN) card or modem to provide communications with relevant informational channels.

Network connection 1213 transfers data through one or several communication network to other devices. For example, network connection 1213 may be made with another computer through local network 1214 (for example, LAN) or device which is controlled by service provider through communication network 1215. Thus, CS 1201 can transfer and receive information through networks 1214 and 1215, network connection 1213 or network interface 1212. Besides, network connection 2113 may be made through LAN 1214 with mobile device 1216, for example, a pocket computer, laptop or communicator.

The computer system can also be supplied with software (SW) which can be kept on one or several storage/transmitting devices. Such software controls CS 1201, other devices which are provided by the invention, and also gives possibility for CS 1201 to interact with the user. Besides, software can include device drives, operation system, software development tools and other specialized program products.

Figure 9:
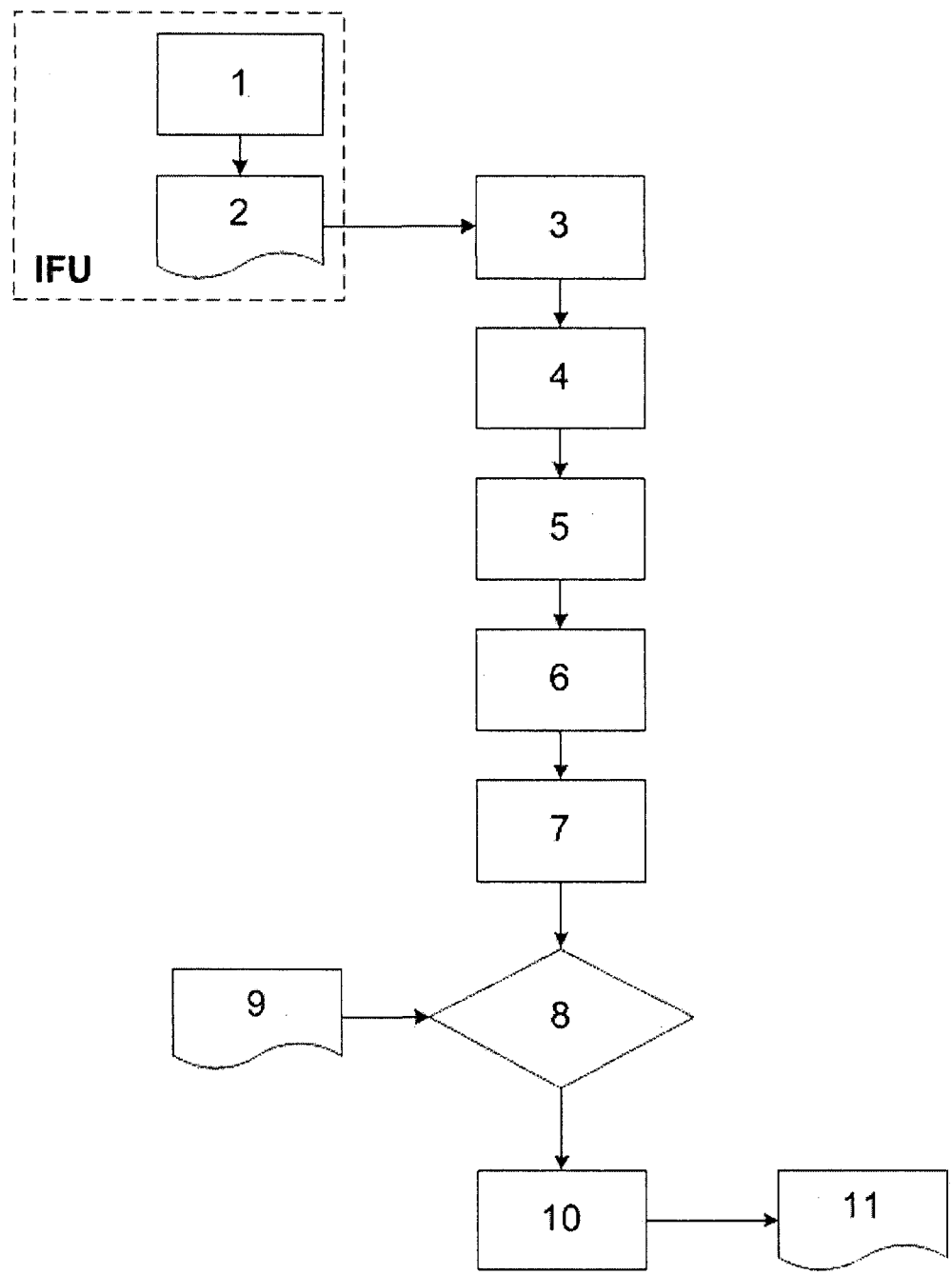
FIG. 9. Operational algorithm of software.

According to the present invention, software can include any interpretable or executable computer codes, including, for example, scripts, dynamic link library (DLL), Java scripts or full executable programs. In particular, one of the main functions of software is to manage all stages of clonal analysis and further diagnosis/conclusion, according to the algorithm presented on FIG. 9.

In accordance with the proposed algorithm, software performs the following sequence of actions, which can be performed by separate program units:

1. Development of a digital image of colonies (1)—this function includes: switching-on a device (scanner), warming-up the device, preliminary scanning and final scanning the selected fragment, and transmitting the digital image for subsequent processing. As a result of the operation, an electronic colony image is formed which is transmitted to CS for further processing.
2. Extraction of a background signal (3)—is the first stage of the mathematical image processing to remove a background signal for the alignment (normalization) of a staining intensity range for colonies which were obtained at different times. The operation can be performed by using various mathematical methods, including a rolling ball method with a radius value of not more than 50 pixels or, more preferably, a sliding paraboloid method with the analogous value.
3. Detection of colony margins (4)—at this stage, a space taken by each colony is separated from the rest of the digital image field not occupied by the colonies. A such operation can be carried out, for example, by using known methods of margin detection between two variously stained zones and determination of object margins. Filtration operations which are performed according to the Sobel, Laplace, Previte, and/or Roberts methods could give good results. To determine colony margins more reliably and precisely, such specific mathematical methods are used, for example, which are based on fractal geometry.
4. Removal of image artifacts (5)—at this stage of the image processing, all artifacts are removed which can prevent correct colony calculations and bias the number of observed colonies, and their morphological and metric characteristics. Such artifacts can include stains of a dried dye, irregularities and signs of a technical labeling on the surface of culture plastic, dust and other pollutions. The operation can be performed by erasing any image which lies outside the colonies found in the previous stage.
5. Colony counting and determination of their morphometric characteristics (6)—a goal of this stage is to obtain the main characteristics of cell colonies which are required for the evaluation of the proliferative and regenerative potentials. The number of colonies is defined as the number of discrete objects which are detected on the previous stages of the image processing. Thus, when necessary, the size of objects can be limited by such parameters as area, perimeter, quadrature, etc., to consider only those colonies which meet specified selection criterion (for example, size, form, density, etc.).
6. Report generation with the results of the measurements (7)—at this stage, a standard report is generated which is based on the primary parameter values obtained in the previous stage. Such primary parameters include values which are obtained directly as a result of the measurements, e.g., the number of colonies, area of each colony, mean optical density of each colony, etc. If necessary, at the stage, additional calculations of derived values are conducted which can be used for calculation of the parameters which characterize the regenerative and proliferative potentials. Such derivative parameters can include CFE-f, specific optical density of each colony, etc.
7. Comparison of the calculated parameters with the normal values (8) kept in a database (9)—at this stage, the calculated parameters are compared with the normal values which are kept in the memory of CS.
8. Generation of conclusions and recommendations regarding treatment/prophylaxis (10)—at this stage, the program generates a conclusion (11) or recommendation based on the results of comparison of the calculated parameters and their normal (mean) values. This operation can be performed by comparing a set of the prespecified conclusions (recommendations) which are kept in the permanent memory of CS, and the results of the comparison performed in the previous stage. To conduct a more flexible and precise diagnosis, it is also possible to use more complex logical operations, including technologies of neural networks or the artificial intellect.

The proposed methods of diagnosis are universal and allow evaluation of the regenerative abilities of primary tissue (and organ) without complex and expensive instrumental studies, by means of clonal analysis of any substrate-dependent cells from the human body. The present invention allows obtaining objective quantitative characteristics of both the regenerative and proliferative potentials of tissue (and organ).

The invention claimed is:

1. A method of determining tissue regenerative ability of the skin of a subject, comprising:
    (i) cultivating skin fibroblast colonies from the subject at conditions which provide formation of discrete colonies applicable for visualization,
    (ii) determining efficacy of colony formation as a parameter that defines regenerative potential of a fibroblast population,
wherein the efficacy of colony formation is calculated as a ratio of the formed cells with the number of cells >20 to the total number of explanted cells, and if efficacy of colony formation is less than 45% for men and 36% for women, low regenerative potential is determined; if efficacy of colony formation is in the range 45-49% for men and 36-45% for women, normal regenerative potential is determined, and if efficacy of colony formation is more than 49% for men and 45% for women, high regenerative potential is determined; and
    (iii) determining percentages of dense and diffuse colonies in cell culture, as a parameter that defines proliferative cell potential,
wherein the dense colonies are characterized by mean of optical density >46 relative units (rel.un.), and the diffuse colonies are ≤25 rel.un. and if percentage of the dense colonies is less than 44%, and percentage of the diffuse colonies is more than 25% for men, and percentage of the dense colonies is less than 40%, and percentage of the diffuse colonies is more than 40% for women, low proliferative potential is determined, if percentage of the dense colonies is in the range 44-54%, and percentage of the diffuse colonies is in the range 20-25% for men, and percentage of the dense colonies is in the range of 40-50%, percentage of the diffuse colonies is in the range 30-40% for women, normal proliferative potential is determined; if percentage of the dense colonies is more than 54%, and percentage of the diffuse colonies is less than 20% for men, and percentage of the dense colonies is more than 50%, and percentage of the diffuse colonies is less than 30% for women, high proliferative potential is determined; and
wherein a low regenerative potential and/or a low proliferative cell potential of the fibroblast population is indicative of abnormal tissue regenerative ability and a high regenerative potential and a high proliferative cell potential of the fibroblast population is indicative of quick tissue regenerative ability.

2. A method of determining tissue regenerative ability of the skin of a subject, comprising:

(i) cultivating skin fibroblast colonies from the subject at conditions which provide formation of discrete colonies applicable for visualization, (ii) determining efficacy of colony formation as a parameter that defines regenerative potential of a fibroblast population, wherein the efficacy of colony formation is calculated as a ratio of the formed cells with the number of cells >20 to the total number of explanted cells, and if efficacy of colony formation is less than 45% for men and 36% for women, low regenerative potential is determined; if efficacy of colony formation is in the range 45-49% for men and 36-45% for women, normal regenerative potential is determined, and if efficacy of colony formation is more than 49% for men and 45% for women, high regenerative potential is determined; and (iii) determining percentages of dense, mixed and diffuse colonies in cell culture and a proliferation index, as parameters that define proliferative cell potential, wherein proliferation index is defined by formula PI=[1(PD)+2(PM)+3(PS)]/100(%), wherein where PI is a proliferation index; PD is the percentage of the diffuse colonies, (%); PM is the percentage of mixed colonies, (%); PS is the percentage of the dense colonies, (%), wherein the dense colonies are characterized by mean optical density >46 rel.un., and the diffuse colonies 25 rel.un., and if proliferative index is less than 2.0 for men and less than 1.8 for women, low proliferative potential is determined; if proliferation index is in the range 2.0-2.4 for men and 1.8-2.0 for women, normal proliferative potential is determined; if proliferation index is more than 2.4 for men and more than 2.0 for women, high proliferative potential is determined; and wherein a low regenerative potential and/or a low proliferative cell potential of the fibroblast population is indicative of abnormal tissue regenerative ability and a high regenerative potential and a high proliferative cell potential of the fibroblast population is indicative of quick tissue regenerative ability.

3. The method according to claim 1, wherein analysis is carried out by using a computer and mathematic modeling to define parameter values which characterize the fibroblast colonies.

4. The method according to claim 2, wherein analysis is carried out by using a computer and mathematic modeling to define parameter values which characterize fibroblast colonies.

* * * * *

UNITED STATES PATENT AND TRADEMARK OFFICE
CERTIFICATE OF CORRECTION

PATENT NO.        : 8,790,890 B2
APPLICATION NO.   : 13/992962
DATED             : July 29, 2014
INVENTOR(S)       : Vadim Leonidovich Zorin et al.

Page 1 of 1

It is certified that error appears in the above-identified patent and that said Letters Patent is hereby corrected as shown below:

On the title page, Item (73), the Assignee's name is incorrect.
Item (73) should read:

-- (73) Assignee: Obshhestvo S Ogranichennoi Otvetstvennost' Yu "Vitacel", Moscow (RU) --

Signed and Sealed this
Twenty-first Day of October, 2014

Michelle K. Lee
*Deputy Director of the United States Patent and Trademark Office*